US008461080B2

(12) United States Patent
Sixl et al.

(10) Patent No.: US 8,461,080 B2
(45) Date of Patent: Jun. 11, 2013

(54) ALUMINUM SILICATE-FREE, HIGHLY CONCENTRATED SUSPENSION CONCENTRATES OF METRIBUZIN

(75) Inventors: Frank Sixl, Rechtsupweg (DE); Udo Bickers, Kelkheim (DE); Harry Koppert, Idstein (DE); Juergen Hopert, Hattersheim (DE)

(73) Assignee: Bayer Cropscience AG, Monheim (DE)

( * ) Notice: Subject to any disclaimer, the term of this patent is extended or adjusted under 35 U.S.C. 154(b) by 245 days.

(21) Appl. No.: 12/854,199

(22) Filed: Aug. 11, 2010

(65) Prior Publication Data

US 2011/0039704 A1 Feb. 17, 2011

Related U.S. Application Data

(60) Provisional application No. 61/234,035, filed on Aug. 14, 2009.

(30) Foreign Application Priority Data

Aug. 14, 2009 (EP) .................................... 09010484

(51) Int. Cl.
| | |
|---|---|
| *A01N 63/00* | (2006.01) |
| *A01N 65/00* | (2009.01) |
| *A01N 43/46* | (2006.01) |
| *A01N 43/707* | (2006.01) |
| *C07D 251/00* | (2006.01) |
| *C07D 253/00* | (2006.01) |

(52) U.S. Cl.
USPC ........... 504/118; 504/189; 504/227; 504/229; 544/180; 544/182; 544/216; 544/219; 544/220

(58) Field of Classification Search
USPC .................. 504/118, 189, 227, 229; 544/180, 544/182, 216, 219, 220
See application file for complete search history.

(56) References Cited

U.S. PATENT DOCUMENTS

| | | | | |
|---|---|---|---|---|
| 4,804,399 | A | 2/1989 | Albrecht et al. | |
| 2011/0166022 | A1* | 7/2011 | Israels et al. .................. | 504/127 |

FOREIGN PATENT DOCUMENTS

| | | | |
|---|---|---|---|
| EP | 0 110 174 | | 6/1984 |
| EP | 0 620 971 | | 10/1994 |
| EP | 1790228 | A1 * | 11/2005 |
| EP | 1790228 | | 3/2007 |
| EP | 1 790 228 | | 5/2007 |
| WO | 2009/021985 | | 2/2009 |
| WO | 2009021985 | | 2/2009 |

OTHER PUBLICATIONS

"Acticide(R) MBS", Google [online], [retrieved May 4, 2012] Retrieved from the Internet: <URL: http://www.kellysolutions.com/erenewals/documentsubmit/KellyData_NE_pesticide_Product Label_67071>.*
International Search Report of PCT/EP2010/004818 dated May 25, 2011.
Manual on Development and Use of FAO and WHO Specifications for Pesticides, Mar. 2006 revision of the First Edition, World Health Organization and Food and Agriculture Organization of the United Nations, Rome, 2006.
Tomlin, C D S, The Pesticide Manual, 2009, Fifteenth Edition, British Crop Production Council, Omega Park. Alton, Hampshire.

* cited by examiner

*Primary Examiner* — Jane C Oswecki
(74) *Attorney, Agent, or Firm* — Baker Donelson Bearman, Caldwell & Berkowitz, PC

(57) ABSTRACT

The invention relates to aqueous, aluminum silicate-free, highly concentrated suspension concentrates, containing the active substance metribuzin, one or more surfactants based on nonionic polymers from the 'acrylic grafted polymers' group, one or more thickeners based on anionic heteropolysaccharides from the xanthan gum group, one or more wetting agents and optionally other components such as antifoaming agents, antifreeze agents and preservatives and other surfactants differing from the aforesaid components.

13 Claims, No Drawings

ALUMINUM SILICATE-FREE, HIGHLY CONCENTRATED SUSPENSION CONCENTRATES OF METRIBUZIN

CROSS REFERENCE TO RELATED APPLICATIONS

This application claims priority to EP application 09010484.5 filed Aug. 14, 2009 and U.S. Application 61/234, 035 filed Aug. 14, 2009, the contents of which are incorporated herein by reference in their entireties.

BACKGROUND OF THE INVENTION

1. Field of the Invention

The invention relates to the technical field of formulations of active substances.

2. Description of Related Art

Active substances can in principle be formulated in a great variety of ways, wherein the properties of the active substances and the nature of the formulation can throw up problems with regard to the producibility, stability, usability and effectiveness of the formulations. In addition, for economic and ecological reasons certain formulations are more advantageous than others.

Water-based formulations, such as aqueous suspension concentrates (SC), as a rule have the advantage that they require a low to zero content of organic solvents. Aqueous suspension concentrates for the formulation of active substances are known from the agrochemicals field. Thus for example aqueous suspension concentrates of pesticides are described in EP 0110174 A. Here a mixture of formaldehyde condensation products or ligninsulfonates and wetting agents is preferably used.

Apart from this, there is in general a demand for highly concentrated formulations of active substances, since the higher concentration has many advantages. Thus for example with highly concentrated formulations a lower expenditure on packaging is necessary than with less concentrated formulations. Similarly, the expenditure for production, transport and storage decreases; also, for example, the preparation of the spraying mixtures is simplified owing to the smaller quantities of for example pesticides which have to be handled, e.g. in the filling and mixing process.

More highly concentrated aqueous suspension concentrates are known, such as for example of sulfur (EP 0220655 A), which is based on mixtures of formaldehyde condensation products, preferably ligninsulfonates and wetting agents.

The active substances from the 1,2,4-triazinones group, such as metamitron and metribuzin, are highly effective herbicides with activity against harmful plants in plant crops. For the active substance metamitron, EP 0620971 A1 describes a more highly concentrated aqueous suspension concentrate based on mixtures of ethoxylated, optionally phosphate group-containing tristyrene- and alkyl-phenols and ligninsulfonate salts. However, the use of these formulation approaches, described in EP 0620971 A1, for the active substance metribuzin did not lead to the desired results. The reasons for this may be on the one hand because metribuzin is less easily wettable than metamitron. EP 1790228 A1 describes how a more highly concentrated aqueous suspension concentrate can be produced for the active substance metribuzin by the use of a mixture of surfactants based on substituted phenol ethers with aluminum silicate-based thickeners, such as for example attapulgite. However, according to reports from the IRAC (International Agency for Research on Cancer), there are possible health risks, depending on the particle length of the attapulgite. Attempts on the basis of the formula of the aluminum silicate-free SC formulation currently on the market, with 480 g metribuzin active substance content/L, which corresponds to 41 weight percent (wt. %), to load this with active substance contents of more than 500 g active substance/L (correspond to ca. 43 wt. %), were unsuccessful. Thus, the milling process by means of bead mills was found to be unworkable since immediate solidification took place.

The task was now to provide formulations for the active substance metribuzin with a high active substance concentration, which are aluminum silicate-free and which have advantageous properties such as storage stability and low viscosity.

As well as this, a stable dispersion in the spray mixture is required, in which the highly diluted active substance concentration must be stable for several hours before application. Such requirements for the stability of dispersions in spray mixtures do not arise at all for formulations for seed treatment (seed dressings, 'seed-treatment formulations or compositions'), since these are applied directly onto the seeds either concentrated or only slightly diluted. Thus publications from this field, such as for example WO 2009/021985 A2, which exclusively relates to 'seed-treatment compositions', provide no suitable technical teaching whatever for the maintenance of stable dispersions in the spray mixture.

SUMMARY OF THE INVENTION

Surprisingly, it has been found that this problem is solved through the aqueous suspension concentrates of the present invention.

A subject of the invention is an aluminum silicate-free, aqueous suspension concentrate, containing the following components (A) 43-61 wt. % of the active substance metribuzin,
(B) 0.5-15 wt. % of one or more surfactants based on nonionic polymers from the 'acrylic grafted polymers' group,
(C) 0.05-0.3 wt. % of one or more thickeners based on anionic heteropoly-saccharides from the xanthan gum group,
(D) 0, 1-10 wt. % of one or more wetting agents,
(E) 0-1 wt. % of one or more antifoaming agents,
(F) 0-20 wt. % of one or more antifreeze agents,
(G) 0-1 wt. % of one or more preservatives,
(H) 0-10 wt. % of one or more other surfactants differing from the aforesaid components.

DETAILED DESCRIPTION OF A PREFERRED EMBODIMENT

The term "aqueous suspension concentrates" is understood to mean water-based suspension concentrates. The water content in the suspension concentrates according to the invention can In general be 20-60 wt. %, preferably 25-35 wt. %; here and in the whole description, unless otherwise defined, the statement "wt. %" (weight percent) relates to the relative weight of the component in question based on the total weight of the formulation.

The active substance metribuzin (component A) is described in "The Pesticide Manual", 14$^{th}$ Edition, The British Crop Protection Council (2006) under the number 573.

The active substance (component A) has a minimum content in the suspension concentrates according to the invention of more than 43 wt. % (correspond to more than 500 g active substance/L), preferably 43-61 wt. % (correspond to 500-760 g active substance/L), particularly preferably 48-57 wt. % (correspond to 550-650 g active substance/L) of the whole formulation.

The surfactants (component B) based on nonionic polymers from the 'acrylic grafted polymers' group are for example nonionic, polymeric surfactants with a "comb" structure, in particular polymethacrylate-methacrylic acid grafted with methoxy-polyethylene oxide.

Examples of such surfactants are inter alia Atlox 4913® and Tersperse 2500®, which are also both preferred.

The content of surfactants (component B) based on nonionic polymers from the 'acrylic grafted polymers' group in the suspension concentrates according to the invention is 0.5-15 wt. %, preferably 2-10 wt. %, particularly preferably 3-6 wt. %.

The thickener (component C) based on anionic heteropolysaccharides from the xanthan gum group is a fermentation product from *Xanthomonas campestris*, in the fermentation medium whereof carbohydrates (such as sugar), a nitrogen source and trace elements and other growth factors are contained. They differ from the aluminum silicate-based thickeners mentioned in EP 1790228 A1 (such as hectorite, montmorillonite, saponite, kaolinite, bentonite, attapulgite etc.) in that they are water-soluble and toxicologically harmless (thus for example xanthan gum is a permitted additive in foodstuffs) and through the property that at lower concentrations (0.05 to 0.5 wt. %) they cause a more effective thickening, in contrast to aluminum silicate-based thickeners, which can be used in higher concentrations (0.1 to 2.5 wt. %)—a property which indeed militates against their use in highly loaded suspension concentrates, since here over-effective thickening immediately leads to undesired solidification.

Examples of thickeners based on anionic heteropolysaccharides from the xanthan gum group are inter alia the Rhodopol® products from Rhodia, which in EP 1790228 A1 were wrongly assigned generically to the aluminum silicate-based thickeners, without further specification of specific products from these. Previously known commercial products from this group are Rhodopol 23®, Rhodopol G®, Rhodopol 50 MD®, Rhodicare T®, Kelzan®, Kelzan S® and Satiaxane CX91®, which are also preferred.

The content of thickeners (component C) based on anionic heteropolysaccharides from the xanthan gum group in the suspension concentrates according to the invention is 0.05-0.30 wt. %, preferably 0.10-0.20 wt. %.

The wetting agents (component D) are for example $C_{10}$-$C_{24}$ alcohols, which can be alkoxylated, e.g. with 1-60 alkylene oxide units, preferably 1-60 EO and/or 1-30 PO and/or 1-15 BO in any order. The terminal hydroxy groups of these compounds can be end-capped with an alkyl, cycloalkyl or acyl residue with 1-24 carbon atoms.

Examples of such wetting agents are inter alia Genapol® C, L, O, T, UD, UDD and X products from Clariant; Plurafac® and Lutensol® A, AT, ON and TO products from BASF, Marlipal® 24 and O13 products from Condea, Dehypon® products from Henkel, Ethylan® products from Akzo Nobel such as Ethylan CD 120 and preparations of ethoxylated fatty alcohols, such as Atlox 4894® from Uniqema, Atlox 4894® is preferred.

The content of wetting agents (component D) in the suspension concentrates according to the invention is 0.1-10 wt. %, preferably 0.2-5 wt. %, particularly preferably 1-3 wt. %.

The antifoaming agents (component E) are for example surface-active compounds based on silicones or silanes such as the "TEGO® Antifoam" range from Evonik and the SE®-, SD®- and SRE® products from Wacker, and the product ranges Bevaloid® from Rhône-Poulenc, Rhodorsil® from Bluestar Silicones, Silcolapse® from ACC and the Dow Corning "Antifoam Emulsions"; and also per- or polyfluorinated surface-active compounds such as Fluowet® products from Clariant, the Bayowet® products from Bayer, the Zonyl® products from DuPont and products of this type from Daikin and Asahi Glass; and acetylene-based ones, such as for example those from Air Products, are possible. Rhodorsil® products, in particular Rhodorsil 454® are preferred.

The content of antifoaming agents (component E) in the suspension concentrates according to the invention is 0-1.5 wt. %, preferably 0.05-1 wt. %, particularly preferably 0.1-0.5 wt. %.

As antifreeze agents (component F), for example, glycol, propylene glycol, glycerin or urea are possible. Propylene glycol is preferred.

The content of antifreeze agents (component F) in the suspension concentrates according to the invention is 0-20 wt. %, preferably 1-15 wt. %, particularly preferably 2-10 wt. %.

As preservatives (component G) bactericidal and fungicidal preparations of substances from the isothiazolinones group are suitable. Examples are the products from the Proxel® range from Arch UK Biocides or from the Acticide® range from Thor Chemie. Acticide MBS® is preferred as the preservative (biocide).

The content of preservatives (component G) in the suspension concentrates according to the invention is 0-1 wt. %, preferably 0.01-0.5 wt. %.

Examples of other surfactants differing from the aforesaid components (component H), wherein EO means ethylene oxide units, PO propylene oxide units and BO butylene oxide units, are listed below:

1) Anionic derivatives of $C_{10}$-$C_{24}$ alcohols, which may be alkoxylated (e.g. with 1-60 alkylene oxide units, preferably 1-60 EO and/or 1-30 PO and/or 1-15 BO in any order, wherein the terminal hydroxy groups of these compounds can be end-capped by an alkyl, cycloalkyl or acyl residue with 1-24 carbon atoms) in the form of ether carboxylates, sulfonates, sulfates and phosphates and inorganic (e.g. alkali metal and alkaline earth) and organic salts thereof (e.g. amine or alkanolamine-based) such as Genapol® LRO, Sandopan® products, or Hostaphat/Hordaphos® products from Clariant.

Copolymers consisting of EO, PO and/or BO units such as for example block copolymers such as the Pluronic® products from BASF and the Synperonic® products from Uniqema with a molecular weight of 400 to $10^8$.

Alkylene oxide adducts of $C_1$-$C_9$ alcohols such as Atlox®5000 from Uniqema or Hoe®-S3510 from Clariant.

2) Fatty add and triglyceride alkoxylates such as the Serdox® NOG products from Condea or alkoxylated plant oils such as soya oil, rape oil, maize oil, sunflower oil, cottonseed oil, linseed oil, coconut oil, palm oil, safflower oil, walnut oil, peanut oil, olive oil or castor oil, in particular rape oil, wherein the plant oils are also understood to mean the transesterification products thereof, e.g. alkyl esters such as rape oil methyl ester or rape oil ethyl ester, for example the Emulsogen® products from Clariant, salts of aliphatic, cyclo-aliphatic and olefinic carboxylic adds and polycarboxylic adds, and alpha-sulfo fatty add esters as obtainable from Henkel.

3) Fatty acid amide alkoxylates such as the Comperlan® products from Henkel or the Amam® products from Rhodia.

Alkylene oxide adducts of alkynediols such as the Surfynol® products from Air Products. Sugar derivatives such as amino and amido sugars from Clariant, glucitols from Clariant, alkylpolyglycosides in the form of the APG® products from Henkel or such as sorbitan esters in the form of the Span®- or Tween® products from Uniqema or cyclodextrin esters or ethers from Wacker.

4) Surface-active cellulose and algin, pectin and guar derivatives such as the Tylose® products from Clariant, the Manutex® products from Kelco and guar derivatives from Cesalpina.

Alkylene oxide adducts based on polyols such as Polyglykol® products from Clariant. Interface-active polyglycerides and derivatives thereof from Clariant.

5) Sulfosuccinates, alkanesulfonates, paraffin- and olefinsulfonates such as Netzer IS®, Hoe® 51728, Hostapur® OS, Hostapur® SAS from Clariant, Triton® GR7ME and GR5 from Union Carbide, Empimin® products from Albright and Wilson, and Marlon®-PS65 from Condea.

6) Sulfosuccinamates such as the Aerosol® products from Cytec or the Empimin® products from Albright and Wilson.

7) Alkylene oxide adducts of fatty amines or quaternary ammonium compounds with 8 to 22 carbon atoms ($C_8$-$C_{22}$) such as for example the Genamin® C, L, O and T products from Clariant.

8) Surface-active, zwitterionic compounds such as taurides, betaines and sulfobetaines in the form of Tegotain® products from Goldschmidt, Hostapon® T and Arkopon® T products from Clariant.

9) Interface-active sulfonamides e.g. von Bayer.

10) Interface-active polyacryl and polymethacryl derivatives such as the Sokalan® products from BASF.

11) Surface-active polyamides such as modified gelatins or derivatized polyaspartic acid from Bayer and derivatives thereof.

12) Surfactant polyvinyl compounds such as modified polyvinylpyrrolidone such as the Luviskol® products from BASF and the Agrimer® products from ISP or the derivatized polyvinyl acetates such as the Mowilith® products from Clariant or the polyvinyl butyrates such as the Lutonal® products from BASF, the Vinnapas® and the Pioloform® products from Wacker or modified polyvinyl alcohols such as the Mowiol® products from Clariant.

13) Surface-active polymers based on maleic anhydride and/or transformation products of maleic anhydride, and copolymers containing maleic anhydride and/or transformation products of maleic anhydride such as the Agrimer®-VEMA products from ISP.

14) Surface-active derivatives of Montan, polyethylene, and polypropylene waxes such as the Hoechst® waxes or the Licowet® products from Clariant.

15) Surface-active phosphonates and phosphinates such as Fluowet®-PL from Clariant.

16) Poly- or perhalogenated surfactants such as for example Emulsogen®-1557 from Clariant.

17) Compounds which are formally the transformation products of the aforesaid phenols with sulfuric acid or phosphoric acid, and neutralized salts thereof with suitable bases, for example the acid phosphate esters of triply ethoxylated phenol, the acid phosphate esters of a nonylphenol reacted with 9 mol of ethylene oxide and the phosphate esters of the reaction product of 20 mol of ethylene oxide and 1 mol of tristyrylphenol neutralized with triethanolamine.

18) Benzenesulfonates such as alkyl- or arylbenzenesulfonates, e.g. acid (poly)alkyl- and (poly)aryl-benzenesulfonates and those neutralized with suitable bases, for example with 1 to 12 C atoms per alkyl residue or with up to 3 styrene units in the polyaryl residue, preferably (linear) dodecylbenzene-sulfonic acid and oil-soluble salts thereof such as for example the calcium salt or the isopropylammonium salt of dodecylbenzenesulfonic acid.

Among the alkyleneoxy units, ethyleneoxy (EO)-, propyleneoxy (PO)- and butyleneoxy (BO)-units, in particular ethyleneoxy units, are preferred.

Ionic emulsifiers and dispersants are also possible, e.g.: polyelectrolytes, such as ligninsulfonates, such as Polyfon® O, Vanisperse® CB or Borresperse® 3A (Borregard).

Examples of surfactants from the group of non-aromatic-based surfactants are the surfactants of the aforesaid groups 1) to 16), preferably of the groups 1), 2), 6) and 8).

Examples of surfactants from the group of aromatic-based surfactants are the surfactants of the aforesaid groups 17) and 18), preferably phenol reacted with 4 to 10 mol of ethylene oxide, commercially available for example in the form of the Agrisol® products (Akcros), nonylphenol reacted with 4 to 50 mol of ethylene oxide, commercially available for example in the form of the Arkopal® products (Clariant), tristyrylphenol reacted with 1 to 50 mol of ethylene oxide, for example from the Soprophor® range (Rhodia) such as Soprophor® FL, Soprophor® 4D-384, and acid (linear) dodecylbenzenesulfonate, commercially available for example in the form of the Marlon® products (Hüls).

Surfactants based on substituted phenol ethers are for example mono-, di-, and preferably trisubstituted phenols, which may be alkoxylated, e.g. ethoxylated and/or propoxylated and/or butoxylated. Herein the number of alkyleneoxy units can be in the range between 1 and 100, preferably 3-60, particularly preferably 5-25. Phenol substituents are preferably styryl or isoalkyl residues. Examples are phenyl-($C_1$-$C_4$) alkyl ethers or (poly)alkoxylated phenols [=phenol-(poly) alkylene glycol ethers], for example with 1 to 50 alkyleneoxy units in the (poly)alkyleneoxy part, wherein the alkylene part preferably has 2 to 4 C atoms, preferably phenol reacted with 3 to 10 mol of alkylene oxide, (poly)alkylphenols or (poly) alkylphenol alkoxylates [=polyalkylphenol (poly)alkylene glycol ethers], for example with 1 to 12 C atoms per alkyl residue and 1 to 150 alkyleneoxy units in the polyalkyleneoxy part, preferably tri-n-butylphenol or triisobutylphenol reacted with 1 to 50 mol of ethylene oxide, polyaryl phenols or polyarylphenol alkoxylates [=polyarylphenol (poly)alkylene glycol ethers], for example tristyrylphenol polyalkylene glycol ethers with 1 to 150 alkyleneoxy units in the polyalkyleneoxy part, preferably tristyrylphenol reacted with 1 to 50 mol of ethylene oxide.

Examples of such surfactants are Soprophor® 3D33, Soprophor® BSU, Soprophor® CY/8 (Rhodia) and Hoe® S3474 and in the form of the Sapogenat® T products (Clariant), for example Sapogenat® T 100.

The content of other surfactants differing from the aforesaid components (component H) in the suspension concentrates according to the invention is 0-10 wt. %.

In a preferred embodiment, the suspension concentrates according to the invention contain:

(A) 43-61 wt % of the active substance metribuzin, (B) 2-10 wt. % of one or more surfactants based on nonionic polymers from the 'acrylic grafted polymers' group, preferably Atlox 4913® and/or Tersperse 2500®, (C) 0.05-0.3 wt. % of one or more thickeners based on anionic heteropoly-saccharides from the xanthan gum group, preferably Rhodopol 23®, Rhodopol G®, Rhodopol 50 MD®, Rhodicare T®, Kelzan®, Kelzan S® and/or Satiaxane CX91®, (D) 0.1-10 wt. % of one or more wetting agents, preferably Atlox 4894®, (E) 0-1 wt. % of one or more antifoaming agents, preferably Rhodorsil 454®, (F) 0-20 wt. % of one or more antifreeze agents, preferably propylene glycol,
(G) 0-1 wt. % of one or more preservatives, preferably Acticide MBS®, and
(H) 0-10 wt. % of one or more other surfactants differing from the aforesaid components.

A particularly preferred embodiment are suspension concentrates according to the invention, wherein there are contained
(A) 48-57 wt. % of the active substance metribuzin,
(B) 2-10 wt. % of one or more surfactants based on nonionic polymers from the 'acrylic grafted polymers' group, preferably 3-6 wt. % Atlox 4913® and/or Tersperse 2500®,
(C) 0.05-0.3 wt. % of one or more thickeners based on anionic heteropoly-saccharides from the xanthan gum group, preferably 0.1-0.2 wt. % Rhodopol 23®, Rhodopol G® Rhodopol 50 MD®, Rhodicare T®, Kelzan®, Kelzan S® and/or Satiaxane CX91®
(D) 0.2-5 wt. % of one or more wetting agents, preferably 1-3 wt. % Atlox 4894®,
(E) 0.05-1 wt. % of one or more antifoaming agents, preferably 0.1-0.5 wt. % Rhodorsil 454®,
(F) 1-15 wt. % of one or more antifreeze agents, preferably 2-10 wt. % propylene glycol,
(G) 0.01-0.5 wt. % of one or more preservatives, preferably Acticide MBS®,
(H) 0-10 wt. % of one or more other surfactants differing from the aforesaid components.

The production of the suspension concentrates according to the invention is effected in known manner (see Winnacker-Küchler, "Chemische Technologie", Vol. 7, C. Hanser Verlag Munich, $4^{th}$ Edn. 1986). During this, firstly the active substance is incorporated by stirring into an aqueous solution, which contains the formulation additives such as dispersant and wetting agents, preservatives, antifoam agents, antifreeze agents and optionally other additives.

The milling of the active substance then as a rule takes place in two steps:
1. (Premilling) Obtention of a particle size of ca. <200 μm by means of colloid mills such as for example gear colloid mills from Probst & Claasen.
2. (Fine milling) Obtention of the finally desired particle size by wet milling, e.g. in bead mills (for example with discontinuous bead mills, such as for example from Drais, or with continuous bead mills, such as for example from Bachofen).

The thickeners based on anionic heteropolysaccharides are incorporated into the finished product after the fine milling step. This takes place either by simply stirring in or, optionally, with the use of high shear forces by means of a colloid mill. In contrast to this, with the use of mineral aluminum silicate thickeners these can be incorporated from the beginning, e.g. together with the active substance and milled therewith via the various milling processes.

The invention also relates to agents obtainable from the suspension concentrate according to the invention by dilution with liquids, preferably water.

It can be advantageous to add to the agents thus obtained further active substances, preferably agrochemical active substances (e.g. as tank mix partners in the form of appropriate formulations) and/or usual aids and additives for application, e.g. self-emulsifying oils such as plant oils or paraffin oils and/or fertilizers. Hence such agents, preferably herbicidal, based on the suspension concentrates according to the invention are also a subject of the present invention.

A particular embodiment of the invention relates to the use of the agents for the control of undesired plant growth, referred to below as "herbicidal agents", obtainable from the suspension concentrates of the present invention.

The herbicidal agents have excellent herbicidal activity against a broad spectrum of economically important mono- and dicotyledonous harmful plants. Even hard-to-control perennial weeds which sprout from rhizomes, rootstocks or other persistent organs are well covered. Here, the herbicidal agents can for example be applied for example in the presowing, preemergence or postemergence method. In particular, by way of example, a few representatives of the mono- and dicotyledonous weed flora may be mentioned, which can be controlled by the herbicidal agents, without it being intended that a restriction to certain species should result from the mentioning.

On the side of the monocotyledonous weed species, for example *Apera spica venti, Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and *Bromus* spp. such as *Bromus catharticus, Bromus secalinus, Bromus erectus, Bromus tectorumn* and *Bromus japonicus* and *Cyperus* species from the annual group, and on the side of the perennial species, *Agropyron, Cynodon, Imperata* and *Sorghum* and also tenacious *Cyperus* species, are well covered.

Among dicotyledonous weed species, the activity spectrum extends to species such as for example *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., on the annual side, and *Convolvulus, Cirsium; Rumex* and *Artemisia* among the perennial weed species.

Harmful plants occurring under the specific cultivation conditions in rice such as for example *Echinochloa, Sagittaria, Alisma, Eleocharis, Scirpus* and *Cyperus* are also outstandingly controlled by the herbicidal agents.

If the herbicidal agents are applied onto the soil surface before germination, then either the emergence of the weed seedlings is completely prevented or the weeds grow to the cotyledon stage, but then cease their growth and finally the out completely after three to four weeks have elapsed.

On application of the herbicidal agents to the green plant parts in the postemergence method, a drastic stop in growth also occurs very rapidly after the treatment and the weed plants remain in the growth stage existing at the time of the application or the out completely after a certain time, so that in this way weed competition harmful to the crop plants is eliminated very early and lastingly.

The herbicidal agents are characterized by a very rapidly developing and long lasting herbicidal action. The rain resistance of the active substances in the herbicidal agents is as a rule good. As particular advantage, it is important that dosages of herbicidal compounds used and effective in the herbicidal agents can be set so low that their soil action is optimally low. Thus not only does their use become possible for the first time in sensitive crops, but also groundwater contamination is practically avoided. Through the combination of active substances according to the invention, a considerable reduction in the dosage of the active substances necessary is rendered possible.

Said properties and advantages are of use in practical weed control, in order to keep agricultural crops free from undesired competitor plants and hence to secure and/or to increase the yields qualitatively and quantitatively. The technical standard is markedly exceeded by these new herbicidal agents with regard to the properties described.

Although the herbicidal agents have excellent herbicidal activity against mono- and dicotyledonous weeds, crop plants of economically significant crops, e.g. dicotyledonous crops such as soya, cotton, rape and sugar-beet, or graminaceous crops such as wheat, barley, rye, oats, millet, rice or maize are only harmed insignificantly or not at all. For these reasons, the present herbicidal agents are very suitable for the selective control of undesired plant growth in agricultural crop plantations or in ornamental plantations.

In addition, the corresponding herbicidal agents have outstanding growth regulating properties in crop plants. They intervene in and regulate the plants' intrinsic metabolism and can thus be used for deliberately influencing substances contained in the plants and for harvest facilitation, such as for example by triggering desiccation and growth suppression. Furthermore, they are also suitable for the general control and inhibition of undesired vegetative growth without in the process killing the plants. With many mono- and dicotyledonous crops, inhibition of the vegetative growth is of great importance, since lodging can thereby be diminished or completely prevented.

Owing to their herbicidal and plant growth regulating properties, the herbicidal agents can also be used for the control of harmful plants in crops of known or still to be developed genetically modified plants. The transgenic plants are as a rule characterized by particular advantageous properties, for example by resistance to certain pesticides, above all certain herbicides, resistance to plant diseases or plant disease pathogens such as certain insects or microorganisms such as fungi, bacteria or viruses. Other particular properties for example relate to the harvest product in terms of quantity, quality, storability, composition and specific component substances. Thus transgenic plants with increased starch content or modified starch quality or those with a different fatty acid composition of the harvest product are known.

The use of the herbicidal agents in economically important transgenic crops of useful and ornamental plants, e.g. of graminaceous crops such as wheat, barley, rye, oats, millet, rice and maize or also crops of sugar-beet, cotton, soya, rape, potato, tomato, peas and other vegetable varieties is preferred. Preferably the herbicidal agents can be used in useful plant crops which are resistant to the phytotoxic effects of the herbicides or have been made resistant by genetic engineering.

In the use of the herbicidal agents in transgenic crops, apart from the effects against harmful plants to be observed in other crops, effects often occur which are specific for the application in the transgenic crop concerned, for example an altered or specifically extended weed spectrum which can be controlled, altered application dosages which can be used for application, preferably good combinability with the other herbicidal active substances against which the transgenic crop is resistant, and influencing of the growth and yield of the transgenic crop plants.

Hence a method for the control of undesired plant growth, preferably in plant crops such as cereals (e.g. wheat, barley, rye, oats, rice, maize or millet), sugar-beet, sugar-cane, rape, cotton and soya, particularly preferably in monocotyledonous crops such as cereals, e.g. wheat, barley, rye, oats and crosses thereof such as triticale, rice, maize and millet, which is characterized in that the herbicidal agents according to the invention are applied onto the harmful plants, plant parts, plant seeds or the surface on which the plants grow, e.g. the cultivation area, is also a subject of the present invention.

The plant crops can also be genetically modified or be obtained by mutation selection and are preferably tolerant towards acetolactate synthase (ALS) inhibitors.

The suspension concentrates according to the invention give improved formulations which are stable in long-term storage and free from application technology problems.

They have low viscosity and associated therewith good flow properties. As a result of this, it is inter alia possible for the user to withdraw precisely metered quantities from a drum. In addition, the low viscosity makes it possible to empty the drums which contain the suspension concentrate according to the invention with no residues.

Additionally and surprisingly, the suspension concentrates according to the invention exhibit outstanding dispersant and stabilizing properties after further dilution with liquids, preferably water.

Thus a stable dispersion is obtained in the spray mixture, in which the highly dilute active substance concentration is stable before the application for several hours.

In this connection, it is astonishing that with the suspension concentrates according to the invention this is achieved with the surfactant based on nonionic polymers from the 'acrylic grafted polymers' group (component B), which serves as the only dispersant, and a very low concentration of the thickener (component C) of 0.05-0.3 wt. %. This is in contrast to the technical teaching from the field of formulations for seed treatment, such as for example WO 2009/021985 A2, which with the use of a combination of two dispersants requires a considerably higher concentration of thickener (>1 wt. %).

EXAMPLES

1. Production 1.1 Formulation Example No. 1 (According to the Invention)

Water is placed in a vat and pumped around a circuit via a colloid mill. The basic components, such as surfactant (e.g. Atlox 4913®) and wetting agent (e.g. Atlox 4894®) and the optional components (formulation aids), such as for example antifoaming agent (e.g. Rhodorsil 450®, antifreeze agent (e.g. propylene glycol) and/or preservative (e.g. Acticide MBS®) and also still further surfactants differing from the aforesaid components are added. As the last component, the active substance is added. After this, the whole mixture is transferred into another vat via the colloid mill. This mixture is then milled by wet milling by means of bead mills. After the wet milling, thickener based on anionic heteropolysaccharides (e.g. Rhodopol 23®) is then incorporated into the finished product by means of a colloid mill with "high-shear" stirring.

1.2 Formulation Examples No. 2 and 3 (State of the Art)

Water is placed in a vat and pumped around a circuit via a colloid mill. The aluminum silicate-based thickeners (e.g. Attagel 40®; Bentone EW®) and other formulation aids, such as for example antifoaming agents (e.g. Rhodorsil 454®), antifreeze agents (e.g. propylene glycol) and/or preservatives (e.g. Acticide MBS®) are added, followed by the surfactants (e.g. Vanisperse CB®, Soprophor CY/8®) and optionally wetting agents (e.g. Hostapon T PHC®). As the final component, the active substance is added. After this, the whole mixture is transferred into another vat via the colloid mill. This mixture is then milled by wet milling by means of bead mills.

In formulation example 3, the main aluminum silicate-based thickener (Attagel 40®) is replaced by a thickener based on anionic heteropolysaccharides (Rhodopol 23®), which is incorporated in the same manner as described in formulation example 1 (after the wet milling).

2. Compositions

TABLE 1

Formulation example Nos. 1-3

| Component | Formulation examples/ component substances | No. 1 according to invention | No. 2 state of the art[2] | No. 3 state of the art[5] |
|---|---|---|---|---|
| A | metribuzin (pure active substance in g/L) | 55.74[1] (600) | 65.03[3] (700) | 65.03[3] (700) |
| B | Atlox 4913 ® | 4.00 | | |
| analog | Vanisperse CB ® | | 2.50 | 1.50 |
| C | Rhodopol 23 ® | 0.15 | | 0.10 |
| analog | Attagel 40 ®[4] | | 0.30 | |
| analog | Bentone EW ®[4] | | 0.10 | 0.10 |
| D | Atlox 4894 ® | 2.00 | | |
| analog | Hostapon T PHC ® | | 0.50 | |
| E | Rhodorsil 454 ® | 0.20 | 0.20 | 0.20 |
| F | propylene glycol | 5.00 | | 2.00 |
| G | Acticide MBS ® | 0.20 | | 0.20 |
| H | Soprophor CY/8 ® | | | 0.50 |
| qs 100 | water | qs 100 | qs 100 | qs 100 |

All data in wt. %
[1] Technical active substance (93.6%) = 52.17% pure active substance
[2] Analogous to formulation examples No. 1 and 2 from EP 1790228 A1
[3] Technical active substance (93.6%) = 60.87% pure active substance
[4] Aluminum silicate-based thickener
[5] Use of a Rhodopol product analogously to the teaching of EP 1790228 A1

3. Test Methods 3.1 Determination of the Viscosity According to CIPAC MT 192

The determination of the viscosities was effected according to CIPAC method MT 192 and determinations were made with a normal commercial rotation viscosimeter from Haake. For the characterization of the flow properties, the viscosities were measured at two different shear rates: at $20^{s-1}$ and at $100^{s-1}$.

3.2 Determination of the Wet Screening Residue

The determination of the wet screening residue was effected according to the CIPAC method MT 59.3 by means of a sieve set with the appropriate mesh sizes.

3.3 Determination of the Particle Size

The determination of the particle size was effected according to the CIPAC method MT 187 by means of laser diffraction analysis.

4. Results

TABLE 2

Physico-chemical data on the suspension concentrates according to the invention (formulation example No. 1)

| Criterion/Measurement parameter | | Initial value | Value after 2 weeks' storage at 54° C. |
|---|---|---|---|
| Viscosity | $20^{s-1}$ [1] | 427 mPas | 424 mPas |
| (CIPAC MT 192) | $100^{s-1}$ [1] | 273 mPas | 249 mPas |
| Wet screening residue | 150 μm[2] | 0% | 0% |
| (CIPAC MT 59.3) | 45 μm[2] | 0.01% | 0.02% |
| Particle size | d(50%)[3] | 3.8 μm | 11.0 μm |
| (CIPAC MT 187) | d(90%)[3] | 9.2 μm | 25.9 μm |

Notes:
[1] Shear rate
[2] Mesh size (and percentage proportion of the residues remaining thereon)
[3] 50 or 90 volume % of all particles lie below the stated diameter Comments: the viscosity of suspension concentrates must on the one hand be sufficiently high to suppress sedimentation of the dispersed active substance particles. On the other hand, efforts should be made to achieve as low a viscosity as possible, and, associated therewith, good flow properties. Thereby the user should be enabled to withdraw precisely metered portions from a drum. In addition, it should be possible to empty drums which contain pesticides, leaving no residues; this requires liquid preparations to have low viscosity. According to experience, the viscosity of suspension concentrates which fulfill the stated requirements lies in the range from about 100 mPas to 500 mPas (measured at $100^{s-1}$). This is entirely fulfilled in an ideal manner by the suspension concentrates according to the invention—even after storage. Apart from this, the further physico-chemical data indicate advantageous properties of the suspension concentrates according to the invention.

TABLE 3

Comparison of viscosity (flow properties)

| Formulation examples/Criterion/ measurement parameter | | No. 1 according to invention | No. 2 state of the art[2] |
|---|---|---|---|
| Viscosity | $20^{s-1}$ [1] | 427 mPas | 1983 mPas |
| (CIPAC MT 192) | $100^{s-1}$ [1] | 273 mPas | 1938 mPas |

Notes:
[1] Shear rate
[2] Analogous to formulation examples No. 1 and 2 from EP 1790228 A1

Comments: in contrast to the viscous formulation of the state of the art (>500 mPas at $100^{s-1}$), the flowability of the suspension concentrate according to the invention is considerably improved because of the low viscosity (between 100-500 mPas at $100^{s-1}$).

TABLE 4

Comparison of the flow properties after storage

| Formulation examples | Flow properties | |
|---|---|---|
| | Initial value | Value after 1 month's storage at 40° C. |
| No. 1 (according to invention) | free-flowing | free-flowing |
| No. 2 (state of the art[1]) | free-flowing (to limited extent) | free-flowing (to limited extent) |
| No. 3 (state of the art[2]) | free-flowing | solidified |

Notes:
[1] Analogous to formulation examples Nos. 1 and 2 from EP 1790228 A1
[2] Use of a Rhodopol product analogously to the teaching of EP 1790228 A1

Comments: in contrast to the suspension concentrate according to the invention, the formulation of the state of the art No. 3 in which a Rhodopol product was used was found not to be storage-stable.

The invention claimed is:

1. An aluminum silicate-free, aqueous suspension concentrate comprising
   (A) 43-61 wt. % of active substance metribuzin,
   (B) 0.5-15 wt. % of at least one surfactant based on at least one nonionic polymer selected from the group consisting of acrylic grafted polymers,
   (C) 0.05-0.3 wt. % of at least one thickener based on at least one anionic heteropoly-saccharide selected from the group consisting of xanthan gums,
   (D) 0.1-10 wt. % of at least one wetting agent,
   (E) 0-1 wt. % of at least one antifoaming agent,
   (F) 0-20wt. % of at least one antifreeze agent,
   (G) 0-1 wt. % of at least one preservative,
   (H) 0-10 wt. % of at least one other surfactant differing from components (A)-(G).

2. The suspension concentrate as claimed in claim 1, comprising
   (A) 43-61 wt. % of the active substance metribuzin,
   (B) 2-10 wt. % of said at least one surfactant based on said at least one nonionic polymer selected from the group consisting of acrylic grafted polymers,
   (C) 0.05-0.3 wt. % of said at least one thickener based on said at least one anionic heteropoly-saccharide selected from the group consisting of xanthan gums,
   (D) 0.1-10 wt. % of said at least one wetting agent,
   (E) 0-1 wt. % of said at least one antifoaming agent,
   (F) 0-20 wt. % of said at least one antifreeze agent,
   (G) 0-1 wt. % of said at least one preservative, and
   (H) 0-10 wt. % of said at least one other surfactant.

3. The suspension concentrate as claimed in claim 1, comprising
   (A) 48-57 wt. % of the active substance metribuzin,
   (B) 2-10 wt. % of said at least one surfactant based on said at least one nonionic polymer selected from the group consisting of acrylic grafted polymers,
   (C) 0.05-0.3 wt. % of said at least one thickener based on at least one anionic heteropoly-saccharide selected from the group consisting of xanthan gums,
   (D) 0.2-5 wt. % of said at least one wetting agent,
   (E) 0.05-1 wt. % of said at least one antifoaming agent,
   (F) 1-15 wt. % of said at least one antifreeze agent,
   (G) 0.01-0.5 wt. % of said at least one preservative,
   (H) 0-10 wt. % of said at least one other surfactant.

4. An agent obtainable from a suspension concentrate as claimed in claim 1 by dilution with a liquid.

5. A suspension concentrate as claimed in claim 1 suitable for the control of undesired plant growth.

6. A method for control of undesired plant growth, comprising applying a suspension concentrate as claimed in claim 1 onto a harmful plant, a plant part, a plant seed and/or a surface whereon plants grow.

7. A suspension concentrate of claim 1, wherein (B) comprises Atlox 4913® and/or Tersperse 2500®, (C) comprises Rhodopol 23®, Rhodopol G®, Rhodopol 50 MD®, Rhodicare T®, Kelzan®, Kelzan S® and/or Satiaxane CX91®
   (D) comprises Atlox 4894®, (E) comprises Rhodorsil 454®,
   (F) comprises propylene glycol, and (G) comprises Acticide MBS®.

8. A concentrate of claim 3, wherein (B) comprises 3-6 wt. % Atlox 4913® and/or Tersperse 2500®, (C) comprises 0.1-0.2 wt. % Rhodopol 23®, Rhodopol G®, Rhodopol 50MD®, Rhodicare T®, Kelzan®, Kelzan S® and/or Satiaxane CX91®, (D) comprises 1-3 wt. % Atlox 4894®, (E) comprises 0.1-0.5 wt. % Rhodorsil 454®, (F) comprises 2-10 wt. % propylene glycol, and (G) comprises Acticide MBS®.

9. An agent of claim 4, wherein said liquid comprises water.

10. An agent of claim 4 that is capable of controlling unwanted plant growth.

11. A method for control of undesired plant growth, comprising applying an agent as claimed in claim 4 onto a harmful plant, a plant part, a plant seed and/or a surface whereon plants grow.

12. A method for the control of undesired plant growth according to claim 6, wherein the applying of said suspension concentrate occurs by spray application.

13. A method for the control of undesired plant growth according to claim 11, wherein the applying of said agent occurs by spray application.

* * * * *